United States Patent

Birkhoelzer et al.

[11] Patent Number: 5,989,188
[45] Date of Patent: Nov. 23, 1999

[54] METHOD AND APPARATUS FOR DETERMINING THE ENERGY BALANCE OF A LIVING SUBJECT ON THE BASIS OF ENERGY USED AND NUTRITION INTAKE

[75] Inventors: Thomas Birkhoelzer, Weisendorf; Volker Schmidt, Erlangen, both of Germany

[73] Assignee: Siemens Aktiengesellschaft, Munich, Germany

[21] Appl. No.: 09/159,868

[22] Filed: Sep. 24, 1998

[30] Foreign Application Priority Data

Sep. 24, 1997 [DE] Germany .......................... 197 42 153

[51] Int. Cl.$^6$ .............................. A61B 10/00; G06F 17/00
[52] U.S. Cl. .......................... 600/300; 128/921; 434/127
[58] Field of Search ................................. 600/300, 301, 600/531, 532; 128/921; 434/127

[56] References Cited

U.S. PATENT DOCUMENTS

| | | | |
|---|---|---|---|
| 5,178,155 | 1/1993 | Mault | 600/531 |
| 5,263,491 | 11/1993 | Thornton . | |
| 5,363,857 | 11/1994 | Howard . | |
| 5,705,735 | 1/1998 | Acorn | 600/531 |
| 5,890,128 | 3/1999 | Diaz et al. | 128/921 |

FOREIGN PATENT DOCUMENTS

WO 97/28738  8/1997  WIPO .

*Primary Examiner*—Eric F. Winakur
*Attorney, Agent, or Firm*—Hill & Simpson

[57] ABSTRACT

In a method and apparatus for determining the energy balance of a living subject on the basis of the energy use and on the basis of nutrition intake, the energy balance is calculated on the basis of a determined energy use of the subject and on the basis of an input of the nutrition intake of the subject via an input unit. This calculation takes place in a calculating unit supplied with a signal corresponding to the energy use, using a value of the calorific value of the food that can be obtained from a memory. A signal corresponding to this energy balance can be generated on a display unit.

32 Claims, 1 Drawing Sheet

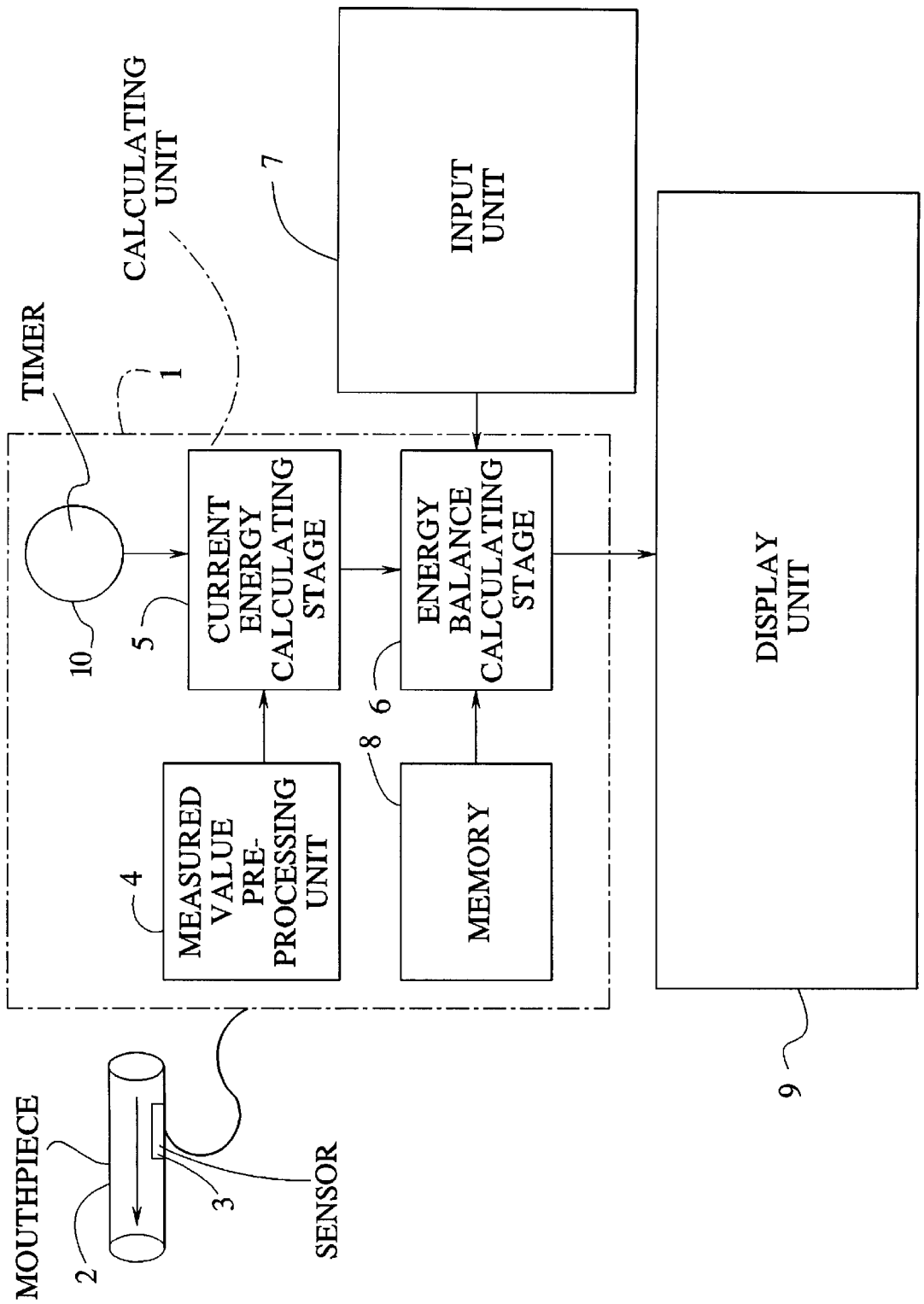

METHOD AND APPARATUS FOR DETERMINING THE ENERGY BALANCE OF A LIVING SUBJECT ON THE BASIS OF ENERGY USED AND NUTRITION INTAKE

BACKGROUND OF THE INVENTION

1. Field of the Invention

The present invention is directed to a method and apparatus for determining the energy balance of a living subject on the basis of energy use and nutrition intake. As used herein, the term "nutrition intake" means nutrition which is currently being supplied to a subject, or nutrition which will be supplied to a subject.

2. Description of the Prior Art

It is known to use calorie tables for weight increase or weight reduction programs, these tables indicating how much energy can be derived respectively from various foods. If, for example, a person would like to achieve a weight reduction, then he sets his nutritional intake such in conjunction with such a table so that the person ingests only a specific number of calories per day.

This method is very complicated; moreover, the "energy use", based on an energy conversion, of the person is not taken into consideration.

SUMMARY OF THE INVENTION

It is an object of the present invention to provide a method and an apparatus wherein it is possible to determine the energy balance of a living subject in a simple way taking the energy use of the subject into consideration.

The above object is achieved in accordance with the principles of the present invention in a method and apparatus for determining the energy balance of a living subject wherein a signal corresponding to the energy use of the subject is supplied to a calculating unit, to which the calorific value of food comprising a nutritional intake of the subject is also supplied, and from the signal corresponding to the energy use and the calorific value, a signal representing the energy balance of the living subject is produced, and is presented on a display unit.

An advantage of the invention is that the energy balance of the living subject is determined in a rather uncomplicated and simple way on the basis of a determined energy use. Such energy use is preferably determined by an indirect calorimetrics calculation in a calculation unit to which the nutrition intake of the subject is supplied, preferably in terms of type and quantity, via an input unit, and based on a signal corresponding to the energy use and a calorific value of the nutrition that can be derived from a memory. As a further advantage, moreover, a signal corresponding to this energy balance is generated on a display, so that the current energy balance status can be monitored at any time.

It is advantageous to determine the energy use from the respiratory air of the subject on the basis of the partial pressures for $O_2$ and $CO_2$. The energy use can thus be determined in an especially simple way that does not disturb the subject.

It is advantageous when the point in time of nutritional ingestion can be entered via the input unit, so that a determination as to when nutrition should be re-supplied can be made dependent on the current activity level.

The energy used overall can be determined in an especially simple way by entering the time duration of a physical activity via the input unit, and the calculating unit determines the energy used overall from the signals of the input unit and the signal of the energy use.

It is also advantageous for the input unit to be able to include information as to whether and to what extent the energy balance should be positive or negative in the data supplied to the calculating unit. It is also useful for the display to indicate whether and when the energy balance is reached and/or downwardly transgressed and/or upwardly transgressed. Monitoring of the energy balance thus is possible in a simple way.

A current weight of the subject can be entered via the input unit and the calculating unit can calculate the anticipated weight of the subject on the basis of the calculated energy balance, so that an anticipated weight increase or weight decrease can be derived at any time. To this end, it is advantageous for the weight to be anticipated also to be shown on the display.

It is also advantageous for selected or available food desired for ingestion to be entered via the input unit so that the calculating unit, taking the desired energy balance into consideration, calculates what quantities of this food can be ingested.

DESCRIPTION OF THE DRAWINGS

The single FIGURE is a schematic block diagram of an apparatus for determining the energy balance of a living subject, constructed and operating in accordance with the principles of the present invention.

DESCRIPTION OF THE PREFERRED EMBODIMENTS

The FIGURE shows an apparatus for determining the energy balance of a living subject on the basis of a determined energy use of the subject and on the basis of an input of the nutrition intake of the subject via an input unit 7. Such an apparatus can, for example, be utilized for weight monitoring and, possibly in a weight reduction or weight increase program. The apparatus has a calculating unit 1 that calculates the energy balance on the basis of an identified energy use of the subject. The energy use of the subject can, for example, be determined and a signal corresponding thereto can be supplied via the input unit 7 to the calculating unit 1. The energy use within a specific time interval and/or the energy use when at rest and/or the energy use under stress and/or the energy use during the normal daily routine, etc., of the subject can form the basis for the calculation. A signal corresponding to the energy use can, for example, be stored in a memory 8 of the calculating unit 1 for this purpose. Preferably, however, a measurement apparatus is provided with which the current energy use or the average energy use of the subject can be determined.

For acquisition of the energy use on the basis of indirect calorimetrics, it is particularly suitable for this purpose to monitor the exhaled air of the subject in view of the $O_2$ and $CO_2$ partial pressures by means of sensors 3, for example via a mouthpiece 2. Additional sensors 3 can be provided for acquiring the temperature and air pressure. The signals of these sensors 3 are supplied via a measured value pre-processing unit 4 to a calculating stage 5 for determining the current energy or calorie use. An energy balance calculation stage 6 for the integration of the measured data, such as for prognosis calculation as well as for diet planning, is supplied with the signals of the calculating module 5 and from the input unit 7.

The calculating stage 6 for integration of the measured data can access the memory 8 in which data corresponding to the nutritional value of foods stored therein are contained. Data allocated to the subject, for example name, weight, height, particularly the desired energy balance, the desired food, start and end of activity and/or meal times, can be entered into the calculating unit 1 via the input unit 7 which may be, for example, a keyboard or touch screen.

A display unit 9 indicates at least the energy balance. The display unit 9 can also indicate one or both of the energy or calorie use in, for example, a freely selectable time interval (minute, hour, day) and/or dependent on the nature and quantity of ingested food with a given energy balance. The display unit 9 can also indicate the duration within which the supplied food is metabolized and/or the weight and/or the anticipated weight of the subject. All of these items can be displayed in writing and/or graphically by the display unit 9. The display unit 9 can be a monitor, a printer and, in a particularly energy saving-way, an LCD or an LED display or the like. Insofar as desired, the display 9 can also be expanded to allow the user data to be displayed. An especially economic apparatus can be realized when the apparatus is implemented, for example, with at least one LED display that transmits a signal dependent on the desired energy balance. It is advantageous for at least three LED displays to be provided and, for example, a green luminous signal to be generated when the desired energy balance is met and a red luminous signal to be generated when the energy balance is downwardly or upwardly transgressed. In order to implement a time-based planning, it is advantageous to supply at least one additional signal from a timer 10 to the calculating unit 1.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for determining an energy balance of a living subject, comprising the steps of:
   obtaining a signal corresponding to energy use of a subject;
   supplying said signal corresponding to energy use to a calculating unit;
   storing respective calorific values for different foods in a memory accessible by said calculating unit;
   entering information identifying nutritional intake of said subject and obtaining a calorific value of food comprising said nutritional intake from said memory and supplying said calorific value to said calculating unit; and
   in said calculating unit, calculating a signal representing an energy balance of said subject from said signal corresponding to energy use and said calorific value of said nutritional intake, and displaying said signal corresponding to the energy balance.

2. A method as claimed in claim 1 wherein the step of obtaining said signal corresponding to energy use comprises monitoring respiratory air of said subject and identifying respective partial pressures of oxygen and carbon dioxide in said respiratory air.

3. A method as claimed in claim 1 wherein the step of obtaining a signal corresponding to energy use by said subject comprises obtaining said signal corresponding to energy use during a steady state condition of said subject.

4. A method as claimed in claim 1 comprising the additional step of entering a time of food ingestion into said calculating unit and using said time of food ingestion to calculate said energy balance.

5. A method as claimed in claim 1 comprising the additional step of identifying a type and quantity of said nutrition intake to said calculating unit and obtaining said calorific value from said memory dependent on said type and quantity.

6. A method as claimed in claim 1 comprising the additional step of entering a time duration of physical activity of said subject into said calculating unit and calculating said energy balance dependent on said time duration of physical activity.

7. A method as claimed in claim 1 comprising the additional step of entering information identifying whether and to what extent said energy balance should be positive or negative as an entered target energy balance, and displaying whether said entered target energy balance is upwardly or downwardly transgressed.

8. A method as claimed in claim 1 comprising the additional steps of entering a current weight of a subject into said calculating unit, and calculating in said calculating unit an anticipated weight of the subject dependent on the energy balance calculated in said calculating unit.

9. A method as claimed in claim 8 comprising the step of displaying said weight.

10. A method as claimed in claim 1 comprising the step of entering a food selected for ingestion into said calculating unit and, in said calculating unit, calculating an amount of said food which can be ingested dependent on the energy balance calculated in said calculating unit.

11. A method as claimed in claim 1 comprising the step of, in said calculating unit, calculating a time span during which no additional nutritional intake can be ingested dependent on a current energy use calculated in said calculating unit and a desired energy balance calculated in said calculating unit.

12. A method for determining an energy balance of a living subject, comprising the steps of:
    obtaining a signal corresponding to energy use of a subject;
    supplying said signal corresponding to energy use to a calculating unit;
    storing respective calorific values for different foods in a memory accessible by said calculating unit;
    entering information identifying nutritional intake of said subject and obtaining a calorific value of food comprising said nutritional intake from said memory and supplying said calorific value to said calculating unit; and
    in said calculating unit, calculating a signal representing an energy balance of said subject from said signal corresponding to energy use and said calorific value of said nutritional intake by determining current energy use by indirect calorimetrics, and displaying said signal corresponding to the energy balance.

13. A method as claimed in claim 12 wherein the step of obtaining said signal corresponding to energy use comprises monitoring respiratory air of said subject and identifying respective partial pressures of oxygen and carbon dioxide in said respiratory air.

14. A method as claimed in claim 12 wherein the step of obtaining a signal corresponding to energy use by said subject comprises obtaining said signal corresponding to energy use during a steady state condition of said subject.

15. A method as claimed in claim 12 comprising the additional step of entering a time of food ingestion into said calculating unit and using said time of food ingestion to calculate said energy balance.

16. A method as claimed in claim 12 comprising the additional step of identifying a type and quantity of said nutrition intake to said calculating unit and obtaining said calorific value from said memory dependent on said type and quantity.

17. A method as claimed in claim 12 comprising the additional step of entering a time duration of physical activity of said subject into said calculating unit and calculating said energy balance dependent on said time duration of physical activity.

18. A method as claimed in claim 12 comprising the additional step of entering information identifying whether and to what extent said energy balance should be positive or negative as an entered target energy balance, and displaying whether said entered target energy balance is upwardly or downwardly transgressed.

19. A method as claimed in claim 12 comprising the additional steps of entering a current weight of a subject into said calculating unit, and calculating in said calculating unit an anticipated weight of the subject dependent on the energy balance calculated in said calculating unit.

20. A method as claimed in claim 19 comprising the step of displaying said anticipated weight.

21. A method as claimed in claim 12 comprising the step of entering a food selected for ingestion into said calculating unit and, in said calculating unit, calculating an amount of said food which can be ingested dependent on the energy balance calculated in said calculating unit.

22. A method as claimed in claim 12 comprising the step of, in said calculating unit, calculating a time span during which no additional nutritional intake can be ingested dependent on a current energy use calculated in said calculating unit and a desired energy balance calculated in said calculating unit.

23. An apparatus for determining an energy balance of a living subject, comprising:
   means for obtaining a signal corresponding to energy use of a subject;
   a calculating unit into which said signal corresponding to energy use is entered;
   means for storing respective calorific values for different foods in a memory accessible by said calculating unit;
   input means for entering information identifying nutritional intake of said subject to said calculating unit, said calculating unit obtaining a calorific value of food comprising said nutritional intake from said memory;
   said calculating unit comprising means for calculating a signal representing an energy balance of said subject from said signal corresponding to energy use and said calorific value of said nutritional intake; and
   display means for displaying said signal corresponding to the energy balance.

24. An apparatus as claimed in claim 23 wherein said means for obtaining said signal corresponding to energy use comprises means for monitoring respiratory air of said subject and for identifying respective partial pressures of oxygen and carbon dioxide in said respiratory air.

25. An apparatus as claimed in claim 23 wherein said input means comprises means for entering a time of food ingestion into said calculating unit and wherein said calculating unit comprises means for using said time of food ingestion to calculate said energy balance.

26. An apparatus as claimed in claim 23 wherein said input means comprises means for identifying a type and quantity of said nutrition intake to said calculating unit and wherein said calculating unit obtains said calorific value from said memory dependent on said type and quantity.

27. An apparatus as claimed in claim 23 wherein said input means comprises means for entering a time duration of physical activity of said subject into said calculating unit and wherein said calculating unit comprises means for calculating said energy balance dependent on said time duration of physical activity.

28. An apparatus as claimed in claim 23 wherein said input means comprises means for entering information identifying whether and to what extent said energy balance should be positive or negative as an entered target energy balance, and wherein said display means comprises means for displaying whether said entered target energy balance is upwardly or downwardly transgressed.

29. An apparatus as claimed in claim 23 wherein said input means comprises means for entering a current weight of said subject into said calculating unit, and wherein said calculating unit comprises means for calculating an anticipated weight of the subject dependent on the energy balance and said weight.

30. An apparatus as claimed in claim 29 wherein said display means comprises means for displaying said weight.

31. An apparatus as claimed in claim 23 wherein said input means comprises means for entering a food selected for ingestion into said calculating unit and, wherein said calculating unit comprises means for calculating an amount of said food which can be ingested dependent on the energy balance.

32. An apparatus as claimed in claim 23 wherein said calculating unit comprises means for calculating a time span during which no additional nutritional intake can be ingested dependent on a current energy use calculated in said calculating unit and a desired energy balance calculated in said calculating unit.

* * * * *